(12) United States Patent
Berlati et al.

(10) Patent No.: US 11,103,474 B2
(45) Date of Patent: Aug. 31, 2021

(54) PHARMACEUTICAL PARENTERAL FORMULATION CONTAINING CARGLUMIC ACID

(71) Applicant: RECORDATI INDUSTRIA CHIMICA E FARMACEUTICA S.P.A., Milan (IT)

(72) Inventors: Fabio Berlati, Rho (IT); Sergio Menegon, Milan (IT); Pierluigi Farina, Milan (IT); Diego Provvedini, Milan (IT); Marco Barchielli, Milan (IT); Alberto Mattei, Milan (IT)

(73) Assignee: RECORDATI INDUSTRIA CHIMICA E FARMACEUTICA S.P.A., Milan (IT)

( * ) Notice: Subject to any disclaimer, the term of this patent is extended or adjusted under 35 U.S.C. 154(b) by 0 days.

(21) Appl. No.: 16/339,591

(22) PCT Filed: Nov. 20, 2017

(86) PCT No.: PCT/EP2017/079738
§ 371 (c)(1),
(2) Date: Apr. 4, 2019

(87) PCT Pub. No.: WO2018/095848
PCT Pub. Date: May 31, 2018

(65) Prior Publication Data
US 2019/0282526 A1    Sep. 19, 2019

(30) Foreign Application Priority Data
Nov. 22, 2016  (EP) .................................... 16199942

(51) Int. Cl.
| | | |
|---|---|---|
| *A61K 31/198* | (2006.01) | |
| *A61K 47/26* | (2006.01) | |
| *A61K 47/18* | (2017.01) | |
| *A61K 9/08* | (2006.01) | |
| *A61K 9/19* | (2006.01) | |
| *A61K 9/00* | (2006.01) | |

(52) U.S. Cl.
CPC .............. *A61K 31/198* (2013.01); *A61K 9/08* (2013.01); *A61K 9/19* (2013.01); *A61K 47/18* (2013.01); *A61K 47/26* (2013.01); *A61K 9/0019* (2013.01)

(58) Field of Classification Search
None
See application file for complete search history.

(56) References Cited

U.S. PATENT DOCUMENTS

| | | | | |
|---|---|---|---|---|
| 2010/0041870 A1* | 2/2010 | Tchessalov | .............. | A61K 9/19 530/350 |
| 2010/0125051 A1* | 5/2010 | Brown | .................... | A61P 35/00 514/4.4 |

FOREIGN PATENT DOCUMENTS

| | | | |
|---|---|---|---|
| CN | 105056246 | | 11/2015 |
| CN | 105056246 A | * | 11/2015 |
| EP | 2 777 696 | | 9/2014 |
| GB | 1112347 | | 5/1968 |
| WO | 2006/079014 | | 7/2006 |

OTHER PUBLICATIONS

English language translation of CN 105 056 246 A (Year: 2015).*
International Search Report dated Dec. 20, 2017 in International (PCT) Application No. PCT/EP2017/079738.
Written Opinion of the International Searching Authority dated Dec. 20, 2017 in International (PCT) Application No. PCT/EP2017/079738.
Extended European Search Report dated May 4, 2017 in corresponding European Application No. 16199942.0.
Lee et al., "N-Carbamoyi-L-Glutamate Plus L-Arginine Can Protect Ammonia Intoxication in Rats with Reduced Functional Liver Mass", Biochemical and Biophysical Research Communications, vol. 248, 1998, pp. 391-394, Article No. RC988984.
Stahl et al., "Handbook of Pharmaceutical Salts Properties, Selection, and Use", International Union of Pure and Applied Chemistry (IUPAC), 2008, 13 pages.
English language translation of Eurasian Office Action, dated Aug. 20, 2020 in corresponding Eurasian Patent Application No. 201991023.

* cited by examiner

*Primary Examiner* — Dominic Lazaro
(74) *Attorney, Agent, or Firm* — Wenderoth, Lind & Ponack, L.L.P.

(57) ABSTRACT

The present invention relates to a pharmaceutical formulation suitable for parenteral administration containing carglumic acid and a buffering agent having a $pK_a$ from 5.5 to 9.0 at 25° C.; according to an embodiment, the buffering agent may have a $pK_a$ from 7.5 to 8.5, preferably a $pK_a$ of about 8.07, such as trometamol. The formulation may also contain at least one bulking agent, such as mannitol. The invention also includes a method for manufacturing a lyophilised sterile formulation by freeze-drying a water solution containing carglumic acid, a buffering agent having a $pK_a$ from 5.5 to 9.0 at 25° C., preferably from 7.5 to 8.5, and optionally a bulking agent to obtain a freeze-dried powder.

12 Claims, No Drawings

PHARMACEUTICAL PARENTERAL FORMULATION CONTAINING CARGLUMIC ACID

The present invention relates to a pharmaceutical formulation suitable for parenteral administration containing carglumic acid and a buffering agent having a $pK_a$ from 5.5 to 9.0 at 25° C.; according to an embodiment, the buffering agent may have a $pK_a$ from 7.5 to 8.5, preferably a $pK_a$ of about 8.07, such as trometamol. The formulation may also contain at least one bulking agent, such as mannitol. The invention also includes a method for manufacturing a lyophilised sterile formulation by freeze-drying a water solution containing carglumic acid, a buffering agent having a $pK_a$ from 5.5 to 9.0 at 25° C., preferably from 7.5 to 8.5, and optionally a bulking agent to obtain a freeze-dried powder.

BACKGROUND

Carglumic acid, whose chemical formula is reported below, is an active principle that is used for the treatment of hyperammonaemia (high blood levels of ammonia).

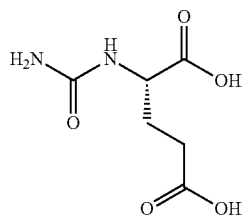 [SMILES: NC(=O)N[C@@H](CCC(=O)O)C(=O)O]

It is marketed in the EU under the trademark Carbaglu® in the form of tablets that must be dispersed in water and ingested immediately or administered by fast push through a syringe via a nasogastric tube, generally in case of hospitalised patients or patients who are not able to swallow.

Carglumic acid is highly hygroscopic and suffers some instability problems. For instance, unopened Carbaglu® containers should be tightly closed and stored at 2 to 8° C. After its first opening, the container must be stored at a temperature above the refrigerated temperature but below 30° C.; furthermore, any unused tablet must be discarded after one month from the first opening.

Processes for manufacturing tablets containing carglumic acid by direct compression are disclosed in EP2777696 and CN105056246.

Due to long term instability of carglumic acid once solubilised, nowadays there are not ready-to-use intravenous or, anyway, injectable sterile formulations on the market containing carglumic acid that could be used for emergency purposes.

DESCRIPTION OF THE INVENTION

The purpose of the present invention is providing a new solid pharmaceutical formulation having a higher content of carglumic acid than Carbaglu®, an improved dissolution profile and improved stability and which, once reconstituted with water, could be administered intravenously, for instance by infusion and/or injection, particularly when a rapid therapeutic effect is needed.

Another purpose of the invention is providing a method for manufacturing said pharmaceutical formulation that does not affect the stability of the active principle itself.

Another purpose of the invention is providing a method for manufacturing said pharmaceutical formulation which may stabilise the obtained sterile dosage form when stored at 2-8° C.

Another purpose of the invention is providing a method for manufacturing said pharmaceutical formulation which may stabilise the obtained sterile dosage form when stored at 25° C.

Which technical problems have been solved by means of a pharmaceutical formulation obtained through a freeze-drying process as discussed below.

Freeze-drying, also known as lyophilisation, is a dehydration process typically used to formulate into a dosage form a perishable or unstable active principle. Freeze-drying works by freezing a water mixture of the active principle together with one or more physiologically acceptable excipients and then reducing the surrounding pressure to allow the frozen water to sublimate directly from the solid phase to the gas phase.

In order to allow an effective and industrially applicable freeze-drying process, the water mixture to be frozen must also be chemically and physically stable and, possibly, should be a clear water solution (crystallization or precipitation should be avoided). An intravenously administrable formulation must also be a clear and sterile water-based solution.

The applicant has performed several tests in order to find the most appropriate conditions for obtaining a clear solution of carglumic acid at high concentrations, which included the use of HCl 0.5 M, NaOH 0.5 M or a phosphate and dextrose buffer; such attempts however failed, since no clear and stable solution of carglumic acid could be achieved.

Nevertheless, as it shall be appreciated from the attached experimental section, trometamine (also known as TRIS), which is a buffering agent having a $pK_a$ from 7.5 and 9.0 at 25° C., surprisingly provided excellent results even at high carglumic acid concentrations. In addition, excellent results in terms of manufacturability and product stability were also surprisingly obtained using mannitol as the bulking agent.

The subject-matter of the present invention is thus represented by a pharmaceutical formulation containing carglumic acid or a pharmaceutically acceptable salt or derivative thereof and a buffering agent having a $pK_a$ from 5.5 to 9.0 at 25° C., preferably a $pK_a$ from 7.5 and 8.5 at 25° C., more preferably a $pK_a$ of about 8.07, such as trometamol.

According to an embodiment of the invention, the formulation may also contain at least one bulking agent, such as, but not limited to mannitol. Other bulking agents that may be used in the formulation of the present invention are lactose, threalose, glycine, dextrane, sucrose, glucose, fructose, sorbitol, inositol.

The pharmaceutical formulation according to the present invention may also contain one or more physiologically acceptable excipients in addition to said buffering agent and said bulking agent.

According to a further embodiment, the carglumic acid: trometamol molar ratio is from 1:1 and 1:2.5, preferably about 1:2.

According to a further embodiment, the weight ratio between carglumic acid and the bulking agent, such as mannitol, is from 25:32 and 25:50, preferably about 25:40.

According to a further embodiment, the pharmaceutical formulation of the present invention may be a powder that should be reconstituted in water before use.

According to another embodiment, each dosage form may contain from 400 to 600 mg of carglumic acid, preferably about 500 mg of carglumic acid; in case of dosage forms intended to be used by patients belonging to the paediatric population, each dosage form may contain from 25 to 200 mg of carglumic acid, preferably about 50 mg of carglumic acid.

According to a further embodiment, the pharmaceutical formulation of the present invention may be a water solution, namely either the mixture that will be subjected to freeze-drying in order to provide the above-mentioned lyophilised product or the solution to be administered intravenously once reconstituted with water; such a water solution preferably has a carglumic acid concentration higher than 2% weight/volume, preferably higher than or equal to 2.5% weight/volume.

According to the best embodiment of the invention, the formulation contains carglumic acid, trometanol and mannitol, the carglumic acid:trometamol molar ratio is from 1:1 and 1:2.5, preferably about 1:2 and the carglumic acid: mannitol weight ratio is from 25:32 and 25:50, preferably about 25:40

The subject-matter of the present invention is also represented by a method for manufacturing a powder, which comprises subjecting to freeze-drying a water solution containing carglumic acid, a buffering agent having a $pK_a$ from 7.5 and 9.0 at 25° C. (such as trometamol) and a bulking agent (such as mannitol) to obtain a freeze-dried powder.

A further subject-matter of the invention is then represented by a method for treating hyperammonaemia which comprises administering the present pharmaceutical formulation to a human in need of such a treatment.

Definitions

Unless otherwise defined, all terms of art, notations and other scientific terminology used herein are intended to have the meanings commonly understood by those of skill in the art to which this disclosure pertains. In some cases, terms with commonly understood meanings are defined herein for clarity and/or for ready reference; thus, the inclusion of such definitions herein should not be construed to represent a substantial difference over what is generally understood in the art.

In particular, the term "physiologically acceptable excipient" herein refers to a substance devoid of any pharmacological effect of its own and which does not produce adverse reactions when administered to a mammal, preferably a human. Physiologically acceptable excipients are well known in the art and are disclosed, for instance in the *Handbook of Pharmaceutical Excipients, sixth edition* 2009, herein incorporated by reference.

The term "Pharmaceutically acceptable salts or derivatives" herein refers to those salts or derivatives which possess the biological effectiveness and properties of the salified or derivatized compound and which and which do not produce adverse reactions when administered to a mammal, preferably a human. The pharmaceutically acceptable salts may be inorganic or organic salts; examples of pharmaceutically acceptable salts include but are not limited to: carbonate, hydrochloride, hydrobromide, sulphate, hydrogen sulphate, citrate, maleate, fumarate, trifluoroacetate, 2-naphthalenesulphonate, and para-toluenesulphonate. Further information on pharmaceutically acceptable salts can be found in *Handbook of pharmaceutical salts*, P. Stahl, C. Wermuth, WILEY-VCH, 127-133, 2008, herein incorporated by reference. The pharmaceutically acceptable derivatives include the esters and the ethers.

The term "bulking agent" herein refers to a physiologically acceptable excipient that increases the volume or the weight of a pharmaceutical formulation keeping its utility or functionality intact.

The term "buffering agent" herein refers to a weak acid or base used to maintain the acidity (pH) of a water solution near a chosen value after the addition of another acid or base.

The term "IV" herein means intravenous injection or intravenously injectable.

The term "ICH conditions" herein refers to the thermohygrometric conditions of storage of Drug Products that are intended for already marketed products or submissions of new Marketing Authorizations (MA), outlined by the International Council on Harmonisation (ICH) guidelines.

The terms "approximately" and "about" herein refers to the range of the experimental error, which may occur in a measurement.

The terms "comprising", "having", "including" and "containing" are to be construed as open-ended terms (i.e. meaning "including, but not limited to") and are to be considered as providing support also for terms as "consist essentially of", "consisting essentially of", "consist of" or "consisting of".

The terms "consist essentially of", "consisting essentially of" are to be construed as a semi-closed terms, meaning that no other ingredients which materially affects the basic and novel characteristics of the invention are included (optional excipients may thus included).

The terms "consists of", "consisting of" are to be construed as closed terms.

The term "paediatric population" herein refers to that part of the population from birth to eighteen years.

Experimental Section

Preliminary Solubility Trials

Preliminary solubility trials have been performed using carglumic acid solutions buffered at pH from 5.0 to 5.7 with NaOH (0.5 M) or phosphate; the test were not successful since the solutions were not stable and gave an unknown degradation product (with molecular ion at 159 [m+H]+ detected in HPLC-mass-spectrometry) not present in the solution of carglumic acid in water.

Carglumic acid solution in HCl 0.5 M also did not result stable up to 24 hours, since two known impurities were detected in concentrations above the accepted limits.

After the failure of the preliminary tests with HCl, NaOH or phosphate, two different approaches were considered to develop a freeze-dried product of carglumic acid for injection (500 mg/vial), namely:

freeze-dried formulation containing carglumic acid and bulking agent to be reconstituted with a diluent containing trometamol as buffering agent;

freeze-dried formulation containing carglumic acid, trometamol and bulking agent.

Initial solubility trials were set up to understand which manufacturing and formulation approach could be more suitable.

a. Carglumic Acid in Water Solution 100 ml of solution were prepared dissolving 2.5 g of carglumic acid in water. A white suspension was obtained. The suspension was stirred for 30 minutes without obtaining a clear solution. The solution was heated at about 45° C. A complete solution was obtained at pH=1.9

Carglumic Acid in Water Solution with Trometamol 100 ml of solution were prepared dissolving 5 g of trometamol in water; 2.5 g of carglumic acid were then added. A clear solution was obtained immediately at room temperature, with pH=8.2

Both formulations were observed after 24 hours storage at RT, 5° C. and −20° C. The results are summarized in table 1.

TABLE 1

| Formulation | Room temperature | 5° C. | −20° C.* |
|---|---|---|---|
| Carglumic acid in water solution | Clear solution | Crystalline precipitate | Powder precipitate |
| Carglumic acid in water solution with trometamol | Clear solution | Clear solution | Clear solution |

*= after thawing

These results demonstrated that the presence of a buffering agent having a $pK_a$ from 7.5 and 9.0 at 25° C., such as trometamol, is essential to obtain a clear and stable lyophilisable solution.

Bulking Agent Selection

The first lyophilisation trial was performed in order to select the bulking agent. Laboratory-scale batches (2000 ml) of placebo solutions containing mannitol and lactose as bulking agents were prepared. 20 ml vials were prepared and lyophilised for each formulation. The quali-quantitative compositions of the formulations are reported in table 2.

Bulk Solution Formulation Screening for pH and Osmolality

Different formulations of carglumic acid (API) and trometamol (TRIS) molar ratio and bulking agent concentrations were prepared in order to measure pH and osmolality at the end of solutions' preparation. The quali-quantitative compositions of the formulations are reported in table 3.

TABLE 3

| Formulation | API:TRIS mg | Bulking agent mg | API:TRIS molar ratio | Bulking agent (g/100 ml) | pH | Osmolality (Osmol/kg) |
|---|---|---|---|---|---|---|
| A | 25:32 | 40 | 1:2 | 4% | 6.55 | 0.582 |
| B | 25:50 | 40 | 1:3 | 4% | 8.31 | 0.763 |
| C | 25:16 | 40 | 1:1 | 4% | 4.02 | 0.477 |
| D | 25:40 | 40 | 1:2.5 | 4% | 7.88 | 0.671 |
| E | 25:35 | 40 | 1:2.2 | 4% | 7.56 | 0.615 |
| F | 25:32 | 20 | 1:2 | 2% | 6.58 | 0.465 |
| G | 25:32 | 10 | 1:2 | 1% | 4.35 | 0.386 |
| H | 25:32 | 5 | 1:2 | 0.5% | 4.77 | 0.316 |
| I | 25:32 | — | 1:2 | — | 4.88 | 0.289 |
| L | 25:33 | 10 | 1:2.1 | 1% | 6.83 | 0.399 |
| M | 25:33 | 5 | 1:2.1 | 0.5% | 6.84 | 0.358 |
| N | 25:33 | — | 1:2.1 | — | 7.04 | 0.341 |

Since the formulation must be intravenously injectable, the pH target should be in the range of 6.5-7.5 while osmolality should be in the range of 0.290-0.600 Osm/Kg when the cake is reconstituted with water for injection. In view of their osmolality and pH, formulations A, F, L, and N were selected for a lyophilisation trial. The results of the lyophilisation trial are summarized in table 4.

TABLE 4

| Formulation | API:TRIS molar ratio | Bulking agent (g/100 ml) | pH | Bulk solution density (g/mL) | Cake Appearance |
|---|---|---|---|---|---|
| A | 1:2 | 4% | 6.70 | 1.031 | White compact |
| F | 1:2 | 2% | 6.47 | 1.024 | Partially collapsed |
| L | 1:2.1 | 1% | 6.99 | 1.021 | Collapsed |
| N | 1:2.1 | — | 7.08 | 1.017 | Collapsed |
| Placebo | — | 4% | 10.88 | — | White compact |

TABLE 2

| Component | 1 ml | 1 vial (20 ml) |
|---|---|---|
| Formula for mannitol placebo | | |
| Mannitol | 40 mg | 800 mg |
| Trometamol | 32 mg | 640 mg |
| HCl 37% | For adjustment to pH = 8 | |
| Water for injection | Qs to 1 ml | Qs to 20 ml |
| Formula for lactose placebo | | |
| Lactose | 40 mg | 800 mg |
| Trometamol | 32 mg | 640 mg |
| HCl 37% | For adjustment to pH = 8 | |
| Water for injection | Qs to 1 ml | Qs to 20 ml |

The appearance of the mannitol formulation at the end of lyophilisation cycle resulted in a white quite compact cake; the lactose formulation appearance was a dark yellow melted cake. Mannitol was thus selected as the preferred bulking agent for carglumic acid formulation development.

Formulation A gave a cake with the desired characteristics. This formulation was reconstituted with 20 ml and 25 ml of water for injection to check osmolality, obtaining a value of 0.569 osml/kg for the formulation reconstituted with 20 ml and a value of 0.444 osml/kg if reconstituted with 25 ml.

Considering the results so far obtained for each formulation, formulation A (with API:trometamol molar ratio 1:2 and mannitol as bulking agent at 4% in solution) was chosen for development.

Additional trials were performed in order to check if it were possible to decrease the osmolality value by a slight reduction of the bulking agent, but the cake appearance was not satisfactory as appeared partially melted.

An additional trial named formulation C (API/trometamol 1:1, mannitol 4%) was performed maintaining the same ratio of API/excipients by a adding the remaining amount of trometamol in the solution of reconstitution in order to optimize and reduce the length of the freeze drying process.

The process parameters and conditions applied for manufacturing formulation A and formulation C are listed in the "Methods" section.

Formulation A and formulation C were further subjected to a HPLC stability test under stressed conditions at 60° C. after 24 and 72 hours; the HPLC method is described in the "Methods" section. The results of the HPLC tests, which are summarized in table 5, showed that formulation A is more stable and presents a lower percentage of impurities than formulation C.

TABLE 5

|  |  | Formulation A | | | Formulation C | | |
|---|---|---|---|---|---|---|---|
| TEST | | T0 | 24 h | 72 h | T0 | 24 h | 72 h |
| Assay (mg/vial) | | 495.5 | 486.8 | 482.6 | 504.7 | 493.3 | 467.5 |
| Assay % nominal | | 99.1 | 97.4 | 96.5 | 100.9 | 98.7 | 93.5 |
| Water content % * | | 2.8 | 1.6 | n.a. | 0.6 | 0.6 | n.a. |
| Impurity/ | RRT | Area % | Area % | Area % | Area % | Area % | Area % |
| Related substance | | *RF | *RF | *RF | *RF | *RF | *RF |
| Glutamic acid | 0.45-0.47 | ND | ND | 0.34 | ND | ND | 0.10 |
| IMP 1 | 1.95-1.93 | 0.01 | 0.08 | 0.26 | 0.10 | 0.89 | 2.31 |
| IMP 2 | 2.24-2.21 | 0.00 | 0.02 | 0.08 | 0.01 | 0.06 | 0.17 |
| IMP 5 | 2.30-2.33 | 0.02 | 0.00 | 0.00 | 0.02 | 0.00 | 0.00 |

*Karl Fischer coulometer, model 684 KF (Metrohm) or equivalent
Legend:
RRT = relative retention time: time of peak elution compared to the time of eluition of the main peak (carglumic acid).
RF = response factor (factor applied to correctly quantify the amount of the impurities)
ND = not detected (peak below the limit of detection of the HPLC method)

Based on the results of the development activities performed, formulation A was considered the most appropriate and then selected for further development.

As reported above, during the freeze drying cycle optimization, different trometamol:API molar ratios were tried so to speed up the process and to optimise the solid state properties as well. Both the carglumic acid:trometamol 1:1 ratio and the 1:2 one showed good manufacturability in terms of process. Despite of this, the further accelerated stability study described above indicates that the formulation with the ratio 1:2 has an improved stability profile if compared to the 1:1 molar ratio. Surprisingly, due to the hygroscopic character of carglumic acid, although the water content of the 1:2 formulation is higher than the one detected in the 1:1 formulation, the chemical stability is better using the 1:2 ratio. Thus, the increased trometamol amount seems to protect the API from degradation triggered by the free water still remaining after process completion.

Stability Study (Technical Batch Under ICH Conditions):

After completion of the development work, a stability study under ICH conditions was also performed to gather data about the long-term (commercial) stability of the selected formulation A. The results obtained up to 12 months with a vial of lyophilized formulation A containing 500 mg of carglumic acid stored at 2-8° C. are summarised in table 6.

TABLE 6

| | Lyophilized Drug Product | | | | | | |
|---|---|---|---|---|---|---|---|
| | | Results | | | | | |
| Test | T0 | 1 Month | 2 Months | 3 Months | 6 Months | 9 Months | 12 Months |
| Appearance | Freeze-dried, white, compact cake | Unchanged | Unchanged | Unchanged | Unchanged | Unchanged | Unchanged |
| Assay mg/vial | 504.7 | 500.4 | 504.1 | 496.6 | 498.2 | 510.1 | 503.1 |
| Assay % | 100.9 | 100.1 | 100.8 | 99.3 | 99.6 | 102.0 | 100.6 |

TABLE 6-continued

| Related Substances % (1)(2) | | | | | | | |
|---|---|---|---|---|---|---|---|
| Specified Related Substances | | | | | | | |
| Glutamic acid RRT0.47 | ND | ND | ND | ND | ND | ND | ND |
| IMP 6 RRT 1.20 | ND | ND | ND | ND | ND | ND | ND |
| IMP 1 RRT 1.93 | <0.10 (0.011) | <0.10 (0.013) | <0.10 (0.008) | <0.10 (0.005) | <0.10 (0.005) | <0.10 (0.006) | <0.10 (0.007) |
| IMP 2 RRT 2.21 | <0.10 (0.003) | <0.10 (0.004) | <0.10 (0.004) | <0.10 (0.002) | <0.10 (0.001) | <0.10 (0.001) | <0.10 (0.001) |
| IMP 5a RRT 2.34 | <0.10 (0.015) | <0.10 (0.015) | <0.10 (0.023) | <0.10 (0.019) | <0.10 (0.019) | <0.10 (0.022) | <0.10 (0.020) |
| IMP 5b RRT 2.77 | ND | ND | ND | ND | ND | ND | ND |
| Each Other Individual Related Substance | ND | ND | ND | ND | ND | ND | |
| Total Related Substances | <0.10 | <0.10 | <0.10 | <0.10 | <0.10 | <0.10 | <0.10 |
| Water Content | 1.4% | 1.5% | 1.3% | 1.4% | 1.4% | 1.3% | 1.5% |

| Reconstituted solution in Sterile Water for Injections | | | | | | | |
|---|---|---|---|---|---|---|---|
| | Results | | | | | | |
| Test | T0 (3) | 1 Month (3) | 2 Months (3) | 3 Months (4) | 6 Months (4) | 9 Months (4) | 12 Months (4) |
| Reconstitution Time | ≈1 min | ≈1 min | ≈1 min | ≈1 min | ≈1 min | ≈1 min | ≈1 min |
| Appearance of Reconstituted Solution | Clear, solution, free from visible particles | Unchanged | Unchanged | Unchanged | Unchanged | Unchanged | Unchanged |
| pH of Reconstituted Solution | 6.3 | 6.3 | 6.3 | 6.4 | 6.3 | 6.3 | 6.3 |

Note (1):
The results <0.10% (LOQ) are reported in brackets only for information.
Note (2):
The Total Related Substances % is the sum of the reportable (≥0.10%) specified and unspecified impurities.
Note (3):
The reconstitution volume is 20 ml
Note (4):
The reconstitution volume is 25 ml The results obtained up to 12 months with a vial of lyophilized formulation A containing 500 mg of carglumic acid stored at 25° C./60% RH are summarised in table 7.

TABLE 7

| Lyophilized Drug Product | | | | | | | |
|---|---|---|---|---|---|---|---|
| | Results | | | | | | |
| Test | T0 | 1 Month | 2 Months | 3 Months | 6 Months | 9 Months | 12 Months |
| Appearance | Freeze dried, white compact cake | Unchanged | Unchanged | Unchanged | Unchanged | Unchanged | Unchanged |
| Assay mg/vial | 504.7 | 495.8 | 508.3 | 498.5 | 499.1 | 509.1 | 503.0 |
| Assay % | 100.9 | 99.2 | 101.7 | 99.7 | 99.8 | 101.8 | 100.6 |

TABLE 7-continued

Related Substances % (1)(2)

Specified Related Substances

| | T0 | 1 Month | 2 Months | 3 Months | 6 Months | 6 Months | 12 Months |
|---|---|---|---|---|---|---|---|
| Glutamic acid RRT 0.47 | ND | ND | ND | ND | ND | ND | ND |
| IMP 6 RRT 1.20 | ND | ND | ND | ND | ND | ND | ND |
| IMP 1 RRT 1.93 | <0.10 (0.011) | <0.10 (0.012) | <0.10 (0.029) | <0.10 (0.017) | <0.10 (0.030) | <0.10 (0.050) | <0.10 (0.055) |
| IMP 2 RRT 2.21 | <0.10 (0.003) | <0.10 (0.004) | <0.10 (0.011) | <0.10 (0.005) | <0.10 (0.007) | <0.10 (0.011) | <0.10 (0.015) |
| IMP 5a RRT 2.34 | <0.10 (0.015) | <0.10 (0.022) | <0.10 (0.021) | <0.10 (0.021) | <0.10 (0.021) | <0.10 (0.019) | <0.10 (0.021) |
| IMP 5b RRT 2.77 | ND | ND | ND | ND | ND | ND | <0.10 (0.012) |
| Each Other Indiv. Relat. Substance | | | | | | | |
| UNK RRT 0.63 | ND | ND | ND | ND | <0.10 (0.050) | <0.10 (0.046) | <0.10 (0.051) |
| UNK RRT 0.87 | ND | ND | ND | ND | <0.10 (0.044) | <0.10 (0.059) | <0.10 (0.050) |
| UNK RRT 1.15 | ND | ND | ND | ND | <0.10 (0.032) | <0.10 (0.050) | <0.10 (0.082) |
| Total Related Substances | <0.10 | <0.10 | <0.10 | <0.10 | <0.10 | <0.10 | <0.10 |
| Water Content | 1.4% | 1.4% | 1.3% | 1.3% | 1.3% | 1.4% | 1.3% |

Reconstituted solution in Sterile Water for Injections

Results

| Test | T0 (3) | 1 Month (3) | 2 Months (3) | 3 Months (4) | 6 Months (4) | 6 Months (4) | 12 Months (4) |
|---|---|---|---|---|---|---|---|
| Reconstitution Time | ≈1 min | ≈1 min | ≈1 min | ≈1 min | ≈1 min | ≈1 min | ≈1 min |
| Appearance of Reconstituted Solution | Clear solution free from visible particles | Unchanged | Unchanged | Unchanged | Unchanged | Unchanged | Unchanged |
| pH Recon. Sol. | 6.3 | 6.3 | 6.3 | 6.3 | 6.3 | 6.3 | 6.3 |

Note (1):
The results <0.10% (LOQ) are reported in brackets only for information.

Note (2):
The Total Related Substances % is the sum of the reportable (≥0.10%) specified and unspecified impurities.

Note (3):
The reconstitution volume is 20 ml

Note (4):
The reconstitution volume is 25 ml

All the chemical and physical results obtained so far are fully matching the specifications required for commercial purposes at both 2-8° C. and 25° C. storage conditions.

Methods
Manufacturing Method:
The freeze drying cycle applied for the manufacturing of both formulation A and formulation C is described below.

Batch size: 2 liters batch

Bulk solution was filled into one tray of 31/39 vials with 20 ml filling volume. One tray was filled with mannitol solution to fully load the freeze-drier and the product lyophilized according to the lyophilization cycle described in table 8.

TABLE 8

| Lyophilization Cycle | Shelves T Set point (° C.) | Set Time (hrs:min) | Actual time (hrs:min) |
|---|---|---|---|
| Freezing (shelves cooling) | −42° C. | 01:00 | 03:00 |
| Freezing (shelves holding) | −42° C. | 06:00 | 06:00 |

TABLE 8-continued

| Lyophilization Cycle | Shelves T Set point (° C.) | Set Time (hrs:min) | Actual time (hrs:min) |
|---|---|---|---|
| Annealing (shelves heating) | −5° C. | 01:20 | 01:00 |
| Annealing (shelves holding) | −5° C. | 04:00 | 04:00 |
| Freezing (shelves cooling) | −40° C. | 00:35 | 02:00 |
| Freezing (shelves holding) | −40° C. | 02:00 | 03:00 |
| Primary drying (shelves heating) | −10° C. | 05:00 | 05:00 |
| Primary drying (shelves holding) | −10° C. | 48:00 | 55:00* |
| Secondary drying (shelves heating) | +35° C. | 03:45 | 04:00 |
| Secondary drying (shelves holding) | +35° C. | 10:00 | 10:00 |
| Secondary drying (shelves heating) | +45° C. | 00:10 | 01:00 |
| Secondary drying (shelves holding) | +45° C. | 10:00 | 10:00 |
| Secondary drying (shelves cooling) | +25° C. | 00:20 | 01:00 |
| Secondary drying (shelves holding) | +25° C. | 24:00** | 15:00 |
| Chamber pressure: 200 μbar | | | |
| Stoppering under partial vacuum: 700 mbar | — | — | |
| Total cycle duration | | | 121 |

*= time needed for the product to reach set up T ° C. = −23° C. to start secondary drying
**= time adjustable (min 2 hours) to unload the freeze drier during working hours At the end of the cycle, the vials were stopped under partial nitrogen (700 mbar) within the freeze-drier chamber and sealed with flip-off caps.

HPLC Method:
Materials and Reagents
Carglumic acid Reference Standard
Deionized water, Milli Q grade or equivalent
Methanol, HPLC grade
$KH_2PO_4$, ACS Reagent
$H_3PO_4$ 85%, ACS Reagent
Equipment
HPLC system Agilent 1100 series or equivalent equipped with UV-VIS detector, cooled auto sampler, degassing system and column oven
Acquisition Data System
HPLC column Develosil 5 μm, RPAQUEOUS-AR C30, 250×4.6 mm or equivalent
Pre-column Gemini C18 or equivalent
Balance accurate to 0.001 mg
High precision laboratory glassware
Chromatographic Conditions
Column temperature: 25° C.
Mobile phase A: $KH_2PO_4$ 50 mM pH 2.0 per $H_3PO_4$ 85%
Mobile hase B: $CH_3OH$
Flow rate: 1.0 ml/min
Injection volume: 50 μl
Autosampler temperature: 5° C.
Detection wavelength: UV at 215 nm
Elution mode: Gradient as reported in table 9

TABLE 9

| TIME (min) | Mobile phase A % | Mobile phase B % |
|---|---|---|
| 0 | 100 | 0 |
| 8 | 100 | 0 |
| 14 | 90 | 10 |
| 28 | 90 | 10 |
| 30 | 100 | 0 |
| 40 | 100 | 0 |

Run Time 40 minutes

Under these conditions the retention time (Rt) of carglumic acid is about 6.6 min. Slight variations of the mobile phase composition and the flow rate may be carried out to provide a suitable elution time and to meet the requirements of the SST

The invention claimed is:

1. A pharmaceutical formulation comprising carglumic acid or a pharmaceutically acceptable salt or derivative thereof, trometamol having a $pK_a$ from 5.5 to 9.0 at 25° C., and mannitol as a bulking agent,
   wherein a molar ratio of the carglumic acid or pharmaceutically acceptable salt or derivative thereof to the trometamol is 1:2; and
   wherein the formulation is obtained as a lyophilized powder from a solution comprising the mannitol at 4% w/v, the carglumic acid or pharmaceutically acceptable salt or derivative thereof, and the trometamol.

2. The pharmaceutical formulation according to claim 1, wherein a weight ratio of the carglumic acid or pharmaceutically acceptable salt or derivative thereof to the mannitol is from 25:32 to 25:50.

3. The pharmaceutical formulation according to claim 1, wherein the formulation is a water solution obtained by suspending the lyophilized powder in water.

4. The pharmaceutical formulation according to claim 3, wherein a carglumic acid concentration is higher than 2% w/v.

5. The pharmaceutical formulation according to claim 1, further comprising one or more physiologically acceptable excipients.

6. The pharmaceutical formulation according to claim 1, wherein a carglumic acid concentration in the solution is higher than 2% w/v.

7. The pharmaceutical formulation according to claim 1, wherein a carglumic acid concentration in the solution is higher than 2.5% w/v.

8. A method for manufacturing the pharmaceutical formulation according to claim 1, the method comprising freeze-drying a solution comprising carglumic acid or a pharmaceutically acceptable salt or derivative thereof, trometamol having a $pK_a$ from 5.5 to 9.0 at 25° C., and mannitol as a bulking agent at 4% w/v,
   wherein a molar ratio of the carglumic acid or pharmaceutically acceptable salt derivative thereof to the trometamol is 1:2.

9. A method for treating hyperammonaemia, comprising administering the pharmaceutical formulation according to claim 1 to a patient in need thereof.

10. The method for treating hyperammonaemia according to claim 9, wherein the pharmaceutical formulation comprises from 400 to 600 mg of carglumic acid, and the patient is an adult.

11. The method for treating hyperammonaemia according to claim 9, wherein the pharmaceutical formulation comprises from 25 to 200 mg of carglumic acid, and the patient belongs to the paediatric population.

12. The method for treating hyperammonaemia according to claim 9, wherein the pharmaceutical formulation is administered parenterally.

\* \* \* \* \*